United States Patent
Klaus et al.

(10) Patent No.: US 10,478,577 B2
(45) Date of Patent: Nov. 19, 2019

(54) TRACHEAL APPLICATOR AND CORRESPONDING USE

(71) Applicant: TNI MEDICAL AG, Würzburg (DE)

(72) Inventors: Dieter Klaus, Maulburg (DE); Ewald Anger, Eibelstadt (DE); Peter Urban, Freiburg (DE); Christian Breuter, Kürnach (DE)

(73) Assignee: TNI MEDICAL AG, Würzburg (DE)

( * ) Notice: Subject to any disclaimer, the term of this patent is extended or adjusted under 35 U.S.C. 154(b) by 0 days.

(21) Appl. No.: 16/071,968

(22) PCT Filed: Oct. 6, 2017

(86) PCT No.: PCT/EP2017/075533
§ 371 (c)(1),
(2) Date: Jul. 23, 2018

(87) PCT Pub. No.: WO2018/082864
PCT Pub. Date: May 11, 2018

(65) Prior Publication Data
US 2019/0255273 A1    Aug. 22, 2019

(30) Foreign Application Priority Data
Nov. 4, 2016 (DE) .......................... 10 2016 013 168

(51) Int. Cl.
*A61M 16/04* (2006.01)
*A61M 16/08* (2006.01)
*A61M 16/10* (2006.01)

(52) U.S. Cl.
CPC .... *A61M 16/0465* (2013.01); *A61M 16/0816* (2013.01); *A61M 16/1095* (2014.02); *A61M 2205/3368* (2013.01)

(58) Field of Classification Search
CPC .............. A61M 16/04; A61M 16/0465; A61M 16/0488; A61M 16/0497; A61M 16/0816;
(Continued)

(56) References Cited

U.S. PATENT DOCUMENTS 2,845,928 A * 8/1958 Denton .................. A61M 11/06
128/200.21
3,977,432 A * 8/1976 Vidal .................... A61M 16/06
137/889

(Continued)

FOREIGN PATENT DOCUMENTS

CA        2843533 A1    11/2004
DE   10 2006 019402 A1  10/2007
(Continued)

OTHER PUBLICATIONS

PCT English Language Translation of the International Preliminary Report on Patentability, PCT/EP2017/075533, dated May 16, 2019, 7 pages.
(Continued)

*Primary Examiner* — Kathryn E Ditmer
(74) *Attorney, Agent, or Firm* — Quarles & Brady LLP (57) ABSTRACT

The invention at hand relates to a tracheal applicator for enabling administering high flow therapy to tracheotomy patients, as is known from transnasal insufflation by means of TNI devices and has proven successful. This is attained by an optimized physical simulation of the conditions as available when performing transnasal high flow therapy at the nostril with an inserted prong. The flow of inspiration and expiration flowing through the tracheal applicator is conducted nearly free of turbulences and vortexes owing to further constructive measures while simultaneously preserving an open ventilation system.

10 Claims, 7 Drawing Sheets

(58) Field of Classification Search
CPC ... A61M 16/10; A61M 16/1095; A61M 39/10
See application file for complete search history.

(56) References Cited

U.S. PATENT DOCUMENTS

| | | | |
|---|---|---|---|
| 5,582,161 A | 12/1996 | Kee | |
| 5,690,097 A * | 11/1997 | Howard | A61M 16/10 128/204.25 |
| 5,697,361 A * | 12/1997 | Smith | A62B 7/12 128/204.15 |
| 7,171,962 B1 * | 2/2007 | Bloem | A61M 16/04 128/200.26 |
| 8,677,999 B2 * | 3/2014 | Allum | A61M 16/04 128/204.25 |
| 2009/0139530 A1 | 6/2009 | Landis et al. | |
| 2009/0151724 A1 * | 6/2009 | Wondka | A61M 16/0096 128/204.23 |
| 2010/0132707 A1 | 6/2010 | Muller | |
| 2010/0252042 A1 * | 10/2010 | Kapust | A61M 16/0666 128/204.23 |
| 2014/0094741 A1 * | 4/2014 | Bellisario | A61M 25/003 604/39 |
| 2015/0068519 A1 * | 3/2015 | Bambrilla | A61M 16/0096 128/202.27 |

FOREIGN PATENT DOCUMENTS

| | | |
|---|---|---|
| DE | 212011100071 U1 | 1/2013 |
| EP | 0792631 A1 | 9/1997 |
| WO | 2007121736 A2 | 11/2007 |
| WO | 2008060295 A2 | 5/2008 |
| WO | 2011122964 A1 | 10/2011 |

OTHER PUBLICATIONS

PCT International Search Report, PCT/EP2017/075533, dated Feb. 20, 2018, 5 pages.

* cited by examiner

TRACHEAL APPLICATOR AND CORRESPONDING USE

CROSS-REFERENCE TO RELATED APPLICATIONS

This application represents the national stage entry of PCT International Application No. PCT/EP2017/075533 filed on Oct. 6, 2017, which claims the benefit of German Patent Application No. 10 2016 013 168.3 filed on Nov. 4, 2016, the entire contents of which are incorporated herein by reference for all purposes.

BACKGROUND AND TECHNICAL FIELD OF THE INVENTION

The invention at hand relates to the field of ventilatory support devices, such as transnasal insufflation and tracheotomy systems, specifically to the connection between a tracheotomy patient and a high flow therapy device as is used for transnasal insufflation and is sufficiently known from the state of the art (WO 2008/060 295 A2, DE 10 2006 019 402 A1). In the following, these devices will be referred to as TNI devices (transnasal insufflation devices) for short.

The nasal high flow ventilatory support by means of TNI devices, also referred to as nasal high flow therapy (NHF), is finding more widespread use in intensive care, for it has proven to be a viable alternative to the known oxygen therapy and to positive-pressure ventilation which is used for patients suffering from respiratory insufficiency. Moreover, patients find the open system used in nasal high flow therapy more agreeable than the closed pressure systems with tightly strapped ventilation masks, making the former more widely accepted.

Figure 1:
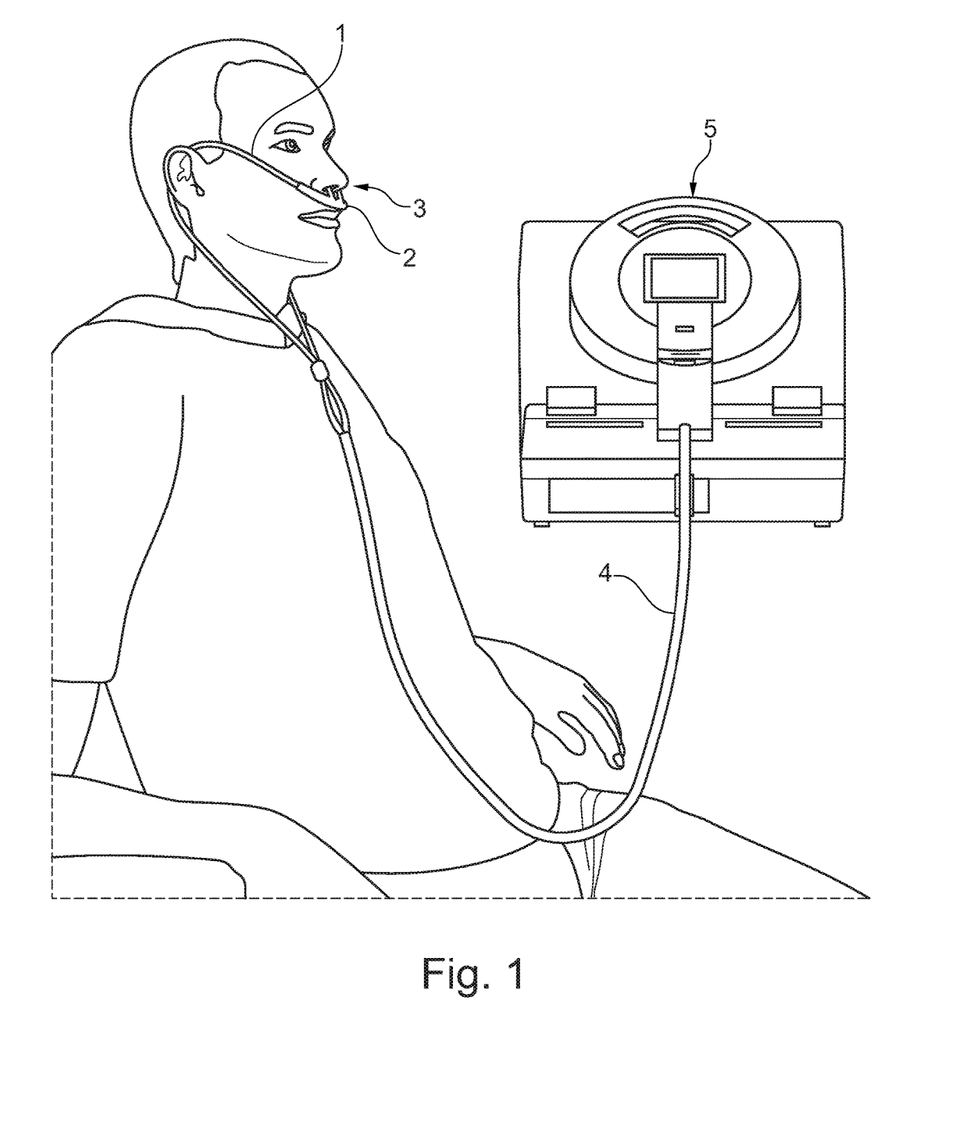
FIG. 1 illustrates a nasal high flow ventilatory support system using a TNI device and a nasal cannula according to the state of the art.

The therapy rests upon the nasal application of a warmed up and wetted air/oxygen mixture $FiO_2$ having a flow rate of 2 to 60 l/min, which is administered into the nostrils (3) coming from a TNI device (5) via a connecting tube (4) and prongs (2) of a nasal cannula (1) (cf. FIG. 1). In this instance, the prongs (2) protrude into the nostrils (3) by approximately 3 mm, with enough space remaining around the prongs (2) so that the unrequired air/oxygen mixture $FiO_2$ and the exhaled spent air can be discharged into the environment in the breathing pauses and during exhalation (open system). Owing to a flow rate set at the TNI device (5), which is typically larger than the patient's peak flow, a stable air/oxygen mixture $FiO_2$ results in the nose, resulting in a consistent supply status for the patient.

When administering a sufficient flow rate, a PEEP (positive end-expiratory pressure) is generated, which has an impact all the way to the alveolar level via the trachea and supports ventilation. This positive physical effect in particular assists the therapy. Nasal secretions and moisture cannot impair the open system as these are also flushed out past the prongs (2) of the nasal cannula (1). The warm and moistened air/oxygen mixture $FiO_2$ thus supports mucociliary cleansing.

In summary, nasal high flow therapy (NHF) is a new and already successfully employed form of therapy with which high oxygen concentrations can be offered, a drying out of the respiratory tracts is prevented, the proportion of the dead space ventilation is reduced and the nasal dead space is washed out. Furthermore, an end-expiratory positive respiratory pressure accumulates when performing the therapy, which counteracts a collapse of the respiratory tracts. Respiratory efficiency is increased and the required respiratory effort is reduced, which contributes to the relief of the respiratory muscle pump. All these advantageous features lead to the anticipation of NHF as the standard therapy used in the fields of respiratory insufficiency, such as chronic respiratory insufficiency, albeit a series of examinations are currently being conducted and first positive findings are available. NHF is a non-invasive ventilatory support which is mainly used for intermitting ventilation.

This differs from the known ventilation via a tracheostoma, in which the patients' breathing is supported via a tracheal cannula inserted into the trachea by piercing through the soft tissue in the neck. This invasive form of artificial ventilation, which is enabled by a surgical procedure, is mostly administered as a continuous long-term ventilation for securing the respiratory tract after accidents and operations or in weaning procedures, albeit this form of artificial ventilation can be interrupted for several hours at a time as long as the tracheotomy patient can endure it. Advantages of tracheotomy are, among other things, a lesser risk of damaging the vocal cords by bypassing the upper respiratory tract and a reduction of the respiratory dead space, which alleviates breathing for the patient.

STATE OF THE ART

In order to be able to use the above-mentioned advantages of NHF for tracheotomy patients as well, tracheal couplings (tracheal connectors, interfaces or applicators) have been developed which couple the respiratory gas ventilator devices available on the market, such as TNI devices (5) or their heated tube systems, to the tracheal cannula of a tracheostoma while taking into consideration the preservation of an open system.

Such connectors are known from prior art documents DE 21 2011 100 071 U1 and CA 2 843 533 A1, respectively, which couple a high flow respiratory gas ventilator system to a tracheal insert. Each connector known from the above-mentioned prior art documents comprises an inlet connection for receiving an incoming gas flow (e.g. an air/oxygen mixture $FiO_2$) coming from a gas source (e.g. a TNI device), an outlet connection as an expiration port for forming an open system as well as a so-called patient connection, which is intended for being connected to a tracheal insert (e.g. a tracheal cannula). In both tracheal couplings known from the above-mentioned prior art documents, the inlet connection is arranged between the patient connection and the outlet connection. The FIGS. 1, 3A to 12 and 17 to 28 of DE 21 2011 100 071 U1 and the state of the art shown in FIGS. 2A, 2B of this document as well as FIGS. 15 and 16 of CA 2 843 533 A1 each show a lateral inlet connection. In the latter, turbulences (vortexes) are generated in the interior of the connectors due to construction, said turbulences being able to be used for throttling the flow during expiration but impairing the draining of secretions and moisture during expiration or when expectorating mucus.

Problem and Solution

It is thus the object of the present invention to create a simply designed tracheal applicator which eliminates the above-mentioned disadvantages. The object is attained by an optimized physical reconstruction of the conditions such as they are available when administering high flow therapy at the nostril with an inserted prong and as they are specified according to the invention by the features described in claim 1. Further useful or advantageous embodiments of the tracheal applicator claimed in claim 1 can be found in the dependent claims 2 to 9. Ventilatory support systems having tracheal applicators according to any one of the claims 1 to 9 are the subject matter of the use claim 10.

Advantages of the Invention

The tracheal applicator (6) claimed in claim 1 at hand is characterized in that it conducts the flow of inspiration and expiration nearly free of turbulences and vortexes owing to its special design while preserving an open system, in that the unrequired air/oxygen mixture $FiO_2$ can be discharged at any time into the environment during the pauses in breathing and during expiration, and in that any produced mucus and secretions can be washed out at any time. Furthermore, the tracheal applicator (6) is easily and quickly exchangeable owing to the conically tapered coupling means available on both sides.

The characterizing feature mentioned in claim 2 advantageously ensures an improved excretion of mucus or secretion since the ventilation openings (25) arranged at the apexes of the elliptical shape are larger and the ventilation opening (25) closest to the constriction (11) promotes the excretion owing to its spout-like shape.

The characterizing feature in claim 3 prevents an outlet opening (22) from being clogged up by an excretion of secretion or mucus since the likeliness of such excretions is largest at the mentioned area due to gravity.

The respective characterizing features of claims 4, 5, 6 and 7 each demonstrate advantageous embodiments of the tracheal applicator (6), which contribute to the prevention of vortexes and turbulences in the gas flows owing to their conductor body properties and shape.

The characterizing constructive feature of claim 8 offers the advantageous prerequisite of being able to choose between the types of production mentioned in claim 9. Should the need arise, the cylindrical contact surface (16) moreover enables easily providing an additional abutment for determining different insertion depths of the connecting piece (9) into the adapter (8).

The characterizing feature in claim 9 discloses different connection options between the adapter (8) and the connecting piece (9) so as to enable different production processes.

Claim 10 demonstrates a beneficial use of the claimed tracheal applicator (6) in a ventilatory support system, whereby the administration of high flow therapies, which have already proven successful in transnasal insufflation, is also enabled for tracheotomy patients.

EXEMPLARY EMBODIMENTS

Starting from a ventilatory support system according to the state of the art illustrated in FIG. 1, exemplary embodiments of the invention, which disclose further advantages and special features, are illustrated in FIGS. 2 to 7 and are described in more detail in the following.

In the figures,

FIG. 4B illustrates in a full-width cut of the tracheal applicator of FIG. 4A taken along the line E-E, FIG. 4C an enlarged detail drawing of the portion delineated by the line A of FIG. 4B.

FIG. 1 illustrates a nasal high flow ventilatory support system having a TNI device (5) and a nasal cannula (1) according to the state of the art for performing a non-invasive ventilation method. The TNI device (5) and the nasal cannula (1) are connected to each other via a heatable connecting tube (4). When administering high flow therapy (NHF), the patient wears a nasal cannula (1) comprising prongs (2), which protrude into the nostrils (3) by approximately 3 mm. Sufficient space remains around the prongs (2) for discharging the unrequired air/oxygen mixture $FiO_2$ and the exhaled spent air into the environment during the pauses in breathing and during exhalation. Therefore, this is referred to as an "open system", which has the advantage of also being able to flush out nasal secretions and moisture past the prongs (2). The TNI device (5) provides the flow volume set at the device for inspiration. Due to therapy related circumstances, a warmed up and moisturized air/oxygen mixture $FiO_2$ having a flow of approximately 60 l/min is administered in this high flow application by the TNI device (5). NHF ventilatory support verifiably leads to improved ventilation, in particular to the reduction in the proportion of dead space ventilation.

Figure 2:
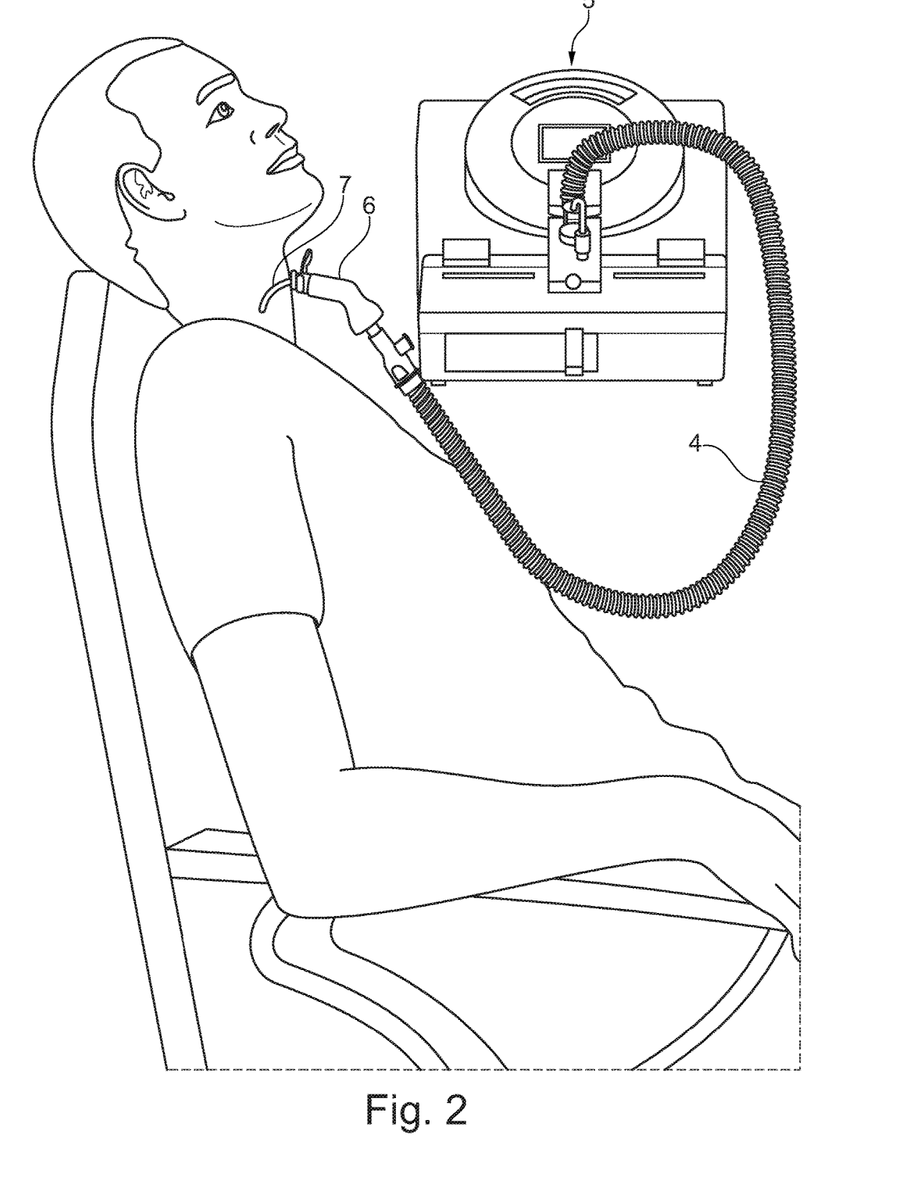
FIG. 2 illustrates a high flow ventilatory support system using a TNI device and a tracheal applicator according to the invention for tracheotomy patients.

FIG. 2 illustrates a high flow ventilatory support system having a TNI device (5) and a tracheal applicator (6) according to the invention for tracheotomy patients. The high flow ventilatory support system enables invasively performing the successful high flow respiration via the tracheal cannula (7) of a tracheostoma. In contrast to nasal insufflation, the tracheal cannula (7) is inserted behind the oropharynx so that the dead space as such is advantageously reduced. The TNI device (5) is connected to the tracheal applicator (6), which itself is plugged onto the tracheal cannula (7), via a heatable connecting tube (4) for this purpose. The tracheal applicator (6) according to the invention having a special design further illustrated in FIGS. 3 to 5 enables using the TNI device (5) with its successful therapy features on a tracheotomy patient.

Figures 3A, 3B:
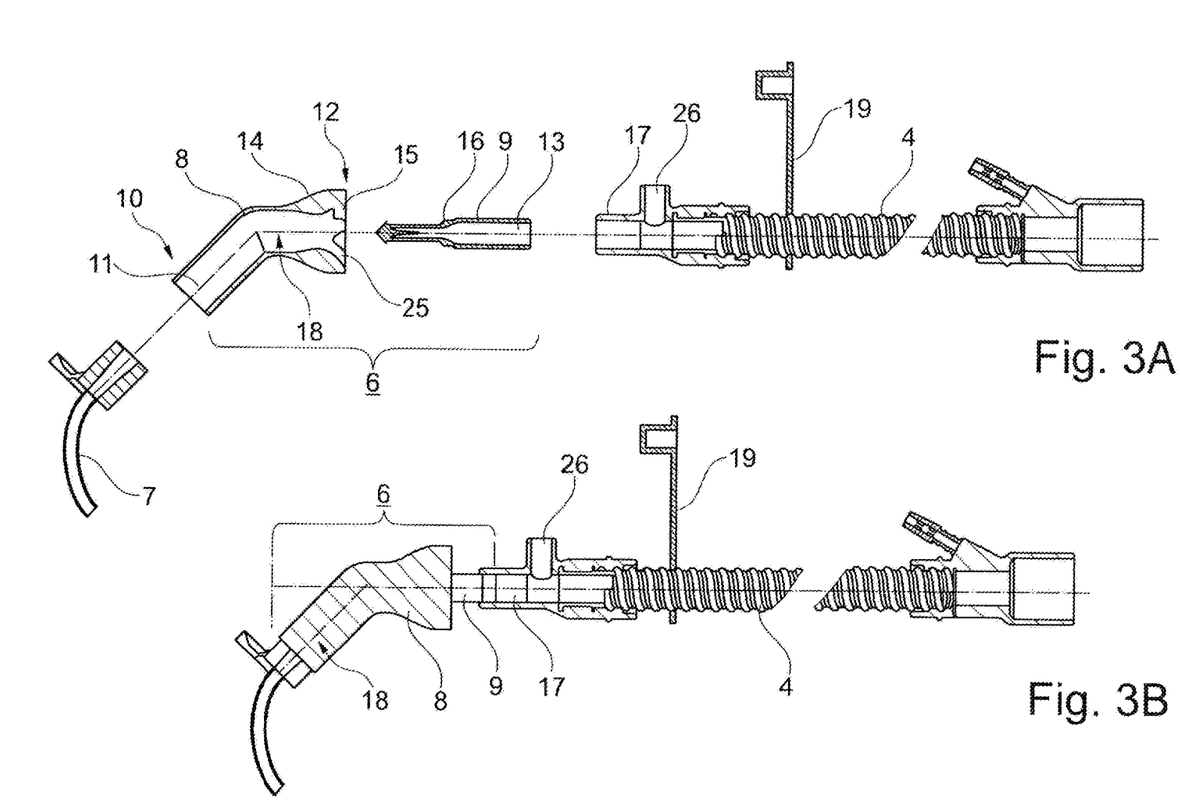
FIG. 3A illustrates a tracheal applicator according to the invention having connections to the TNI device on the tracheal cannula and the connecting tube in an exploded view.
FIG. 3B illustrates a tracheal applicator according to the invention having connections to the TNI device on the tracheal cannula and the connecting tube in an assembled state.

FIG. 3A illustrates the tracheal applicator (6) according to the invention having connections to the TNI device at the tracheal cannula (7) and the connecting tube (4) in an exploded view and FIG. 3B illustrates the tracheal applicator (6) in an assembled state.

Figure 4A:
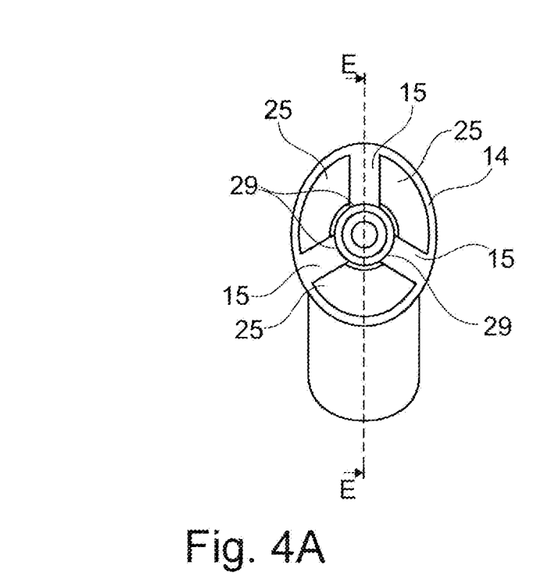
FIG. 4A illustrates a front view of a tracheal applicator according to the invention.

FIG. 3A exemplifies that the tracheal applicator (6) generally comprises a curved or kinked tube-shaped adapter (8) and a connecting piece (9). At the end (10) facing towards the tracheostoma, the adapter (8) has a circular diameter having a conical constriction (11) in the interior for a plug-in connection with the tracheal cannula (7). The connecting piece (9), which can be inserted into and be fixedly secured to the adapter (8) as illustrated in this instance, is arranged at the other end (12) of the adapter (8). For this purpose, the connecting piece (9) is shaped like a rotationally symmetric tube (13) having a cylindrical contact surface (16). The end (12) of the adapter (8) is designed as a trumpet-shaped opening (14), in which three radial crosspieces (15) (cf. FIG. 4) are shaped in such a manner and protrude into the interior in such a manner that they form a three-point reception (29) (cf. FIG. 4), which centrally receives the connecting piece (9) when it is pushed in and holds it by clamping after it has been pushed in or rather pressed in. The adapter (8) and the connecting piece (9) can alternatively be connected by adhesion, welding or can already be produced in one piece (e.g. in a 3D printing process). The rotationally symmetric tube (13) of the connecting piece (9) also has a conic shape at its end towards the connecting tube (4) so that the rotationally symmetric tube (13) is coupled with a tube connection (17) at the end of the connecting tube (4), which leads to a TNI device. Reference numeral (26) at the tube connection (17) refers to an access for a temperature sensor and reference numeral (19) refers to a holder for the heatable connection tube (4), which are commonplace in such systems.

In FIGS. 3A and 3B, the center lines of the enumerated parts are illustrated in dashed lines. The center line (18) of the adapter (8) is illustrated as being angled or kinked so as to highlight the curvature of the adapter (8). The curvature is necessary so that the tracheal cannula (7), when in a plugged-in or assembled state according to FIG. 3B, is mostly free of forces, which come from the tracheal applicator (6) in conjunction with the connecting tube (4). A preferred kink angle of the center line (18) is 60°, albeit other kink angles are better suited and thus conceivable depending on the patient. The holder (19) arranged on the connecting tube (4) additionally works towards keeping forces from acting on the tracheal cannula (7).

Figures 4B, 4C:
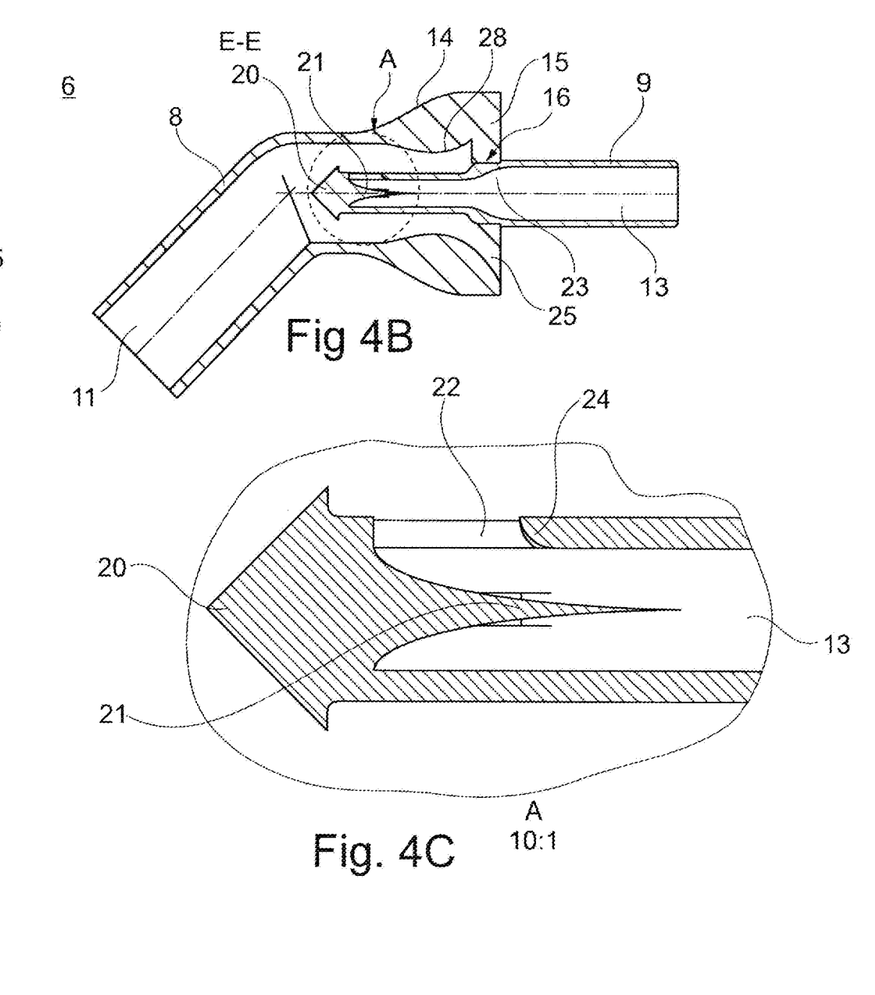

FIG. 4B illustrates a tracheal applicator (6) according to the invention in a full-width section in a sectional view taken along the line E-E as illustrated in the upper left hand image FIG. 4A. It can be seen that the tracheal applicator (6) generally comprises the adapter (8) and the connecting piece (9) fixedly connected thereto. At one end, the curved tube-shaped adapter (8) comprises, as already mentioned, a conical constriction (11), which protrudes into the interior, for a plug-in connection to a tracheal cannula (7) and, at the opposite end, is provided with a trumpet-shaped opening (14), in which three radially extending crosspieces (15) protrude into the interior in such a manner and are shaped at their end such that they form a three-point reception (29) for being fixedly secured to a cylindrical contact surface (16) of the connecting piece (9). Since the crosspieces (15) are each arranged at an offset of 120°, sufficiently large ventilation openings (25) are obtained therebetween for discharging the unrequired air/oxygen mixture $FiO_2$ and the exhaled air as well as for flushing out secretions and mucus in order to prevent stenoses. The connecting piece (9), which is designed as a rotationally symmetric tube (13) constricted in a nozzle-like manner for channeling the $FiO_2$ flow coming from a TNI device, comprises the cylindrical contact surface (16) required for being connected to the adapter (8) and a bottleneck-shaped tapering (23) protruding into the adapter (8) for increasing the flow speed at a consistent $FiO_2$ flow. The bottleneck-shaped tapering (23), which is arranged in the area of the three-point reception (29) and in the interior of the tube (13), has transitions free of tiers, steps or edges for preserving a laminar flow at this position.

The trumpet-shaped opening (14) is shaped via an interior bulge (28) such that the consistent flow volume set at the TNI device (5) can flow from the connecting piece (9) through the adapter (8) into the tracheal cannula (7) nearly free of vortexes upon inspiration.

As can be further seen in FIG. 4B, the end of the connecting piece (9) protruding into the adapter (8) comprises a lid-shaped seal (20), which is conical in the direction of the adapter (8) and comprises a tapered contour (21) in the direction of the tube connection (17) in order to serve as a flow conducting body. As is illustrated in more detail in the detail drawing FIG. 4C taken along the line A of FIG. 4B, this contour (21) can assume the shape of an elliptical or hyperbolical section. In the tube (13), several radially distributed and radially extending outlet openings (22) are provided in direct contact with the seal (20) in order to conduct the air/oxygen mixture $FiO_2$ from the connecting piece (9) into the adapter (8) during the inspiration phase. Preferably, three outlet openings (22) distributed by 90° are available, as can be seen in particular from the sectional progression of the given example in the detail drawing A in FIG. 4C. The cross section of the contour (21) as a flow conducting body can be round, square or polygonal; it depends on the respective number and arrangement of the outlet openings (22). In the given example with the three outlet openings (22), the contour (21) is round. In this detail drawing A, a rounding (24) in the edge of one of the outlet openings (22) of the tube (13) can also be seen; these rounded edges are provided in all outlet openings (22) in order to improve the flow of the air/oxygen mixture $FiO_2$.

The edge of the trumpet-shaped opening (14) is shaped elliptical, as can be seen in the lateral view of the tracheal applicator (6) on the left hand side in FIG. 4. The large axis of the ellipse extends through one of the three crosspieces (15) arranged at an offset of 120° and thus simultaneously extends through the center of one of the three ventilation openings (25)—hereafter referred to as the "lower" ventilation opening—whereby their shape caused by this favors excreting secretion and mucus. As can be further seen from FIG. 4, no outlet opening (22) is provided in the area of the lower ventilation opening (25) since an excretion of mucus could easily clog up an outlet opening (22) in this position.

Figure 5A:
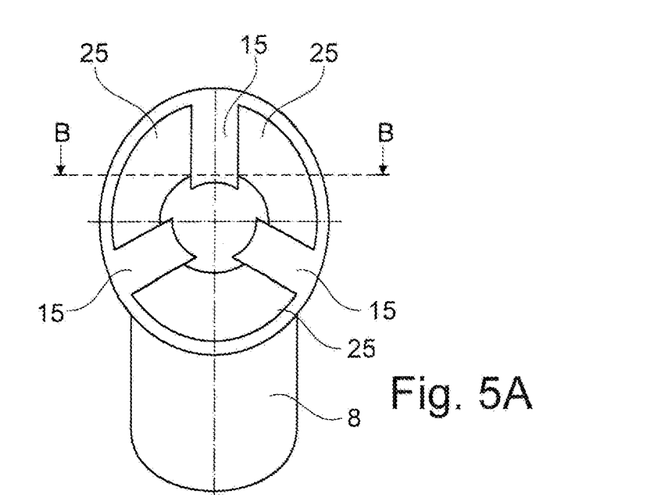
FIG. 5A illustrates a front view of the adaptor of FIG. 4A.
Figures 5B, 5C:
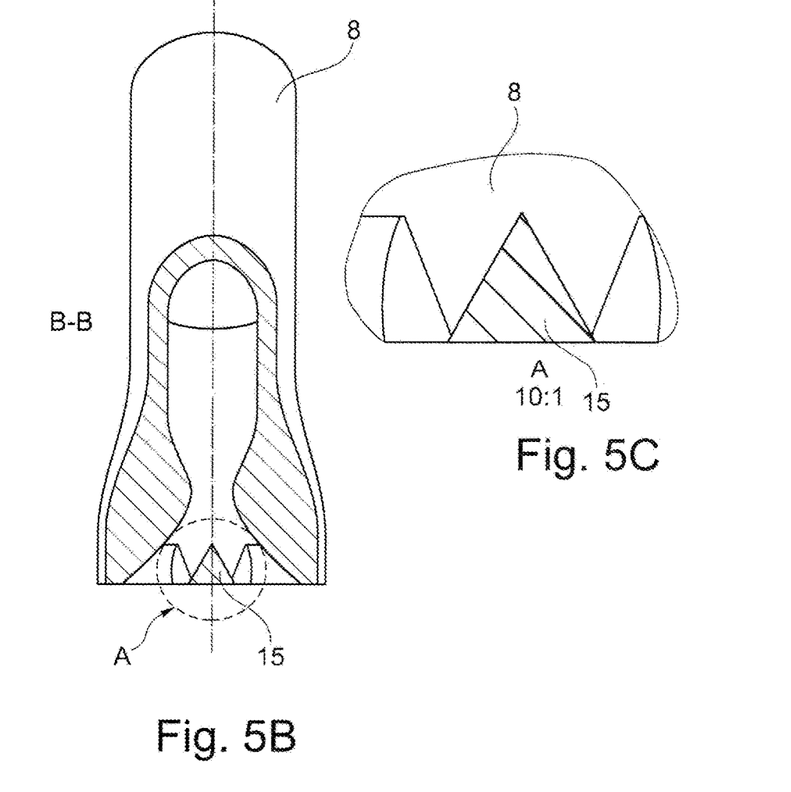
FIG. 5B illustrates a sectional view taken along the line B-B through the adapter according to FIG. 5A.
FIG. 5C illustrates an enlarged detail drawing taken along the line A of FIG. 5B.

FIG. 5B illustrates a sectional view taken along the line B-B through the adapter (8) according to FIG. 5A and FIG. 5C illustrates an enlarged detail drawing taken along the line A of FIG. 5B in which the cross sectional shape of the three crosspieces (15) can be best seen. The three radially extending crosspieces (15) serve not only for connecting the adapter (8) to the connecting piece (9) but also simultaneously form the separating walls between the three ventilation openings (25), as described above. Consequently, they are arranged entirely in the expiration flow as flow resistances and can impede the discharge of breathing air into the environment by producing vortexes. In order to keep the flow resistances as small as possible and to prevent vortexes from forming in the interior of the adapter (8) at this position, the outer surfaces of the crosspieces (15) are shaped tapering towards the interior of the adapter (8), which means they form an acute angle. In the illustrated exemplary embodiment, the cross section of the crosspieces (15) is shaped like an equilateral triangle. Other cross sections are also suitable, e.g. in the shape of acute, equilateral triangles or drop shapes having acute angles.

Figures 6A, 6B:
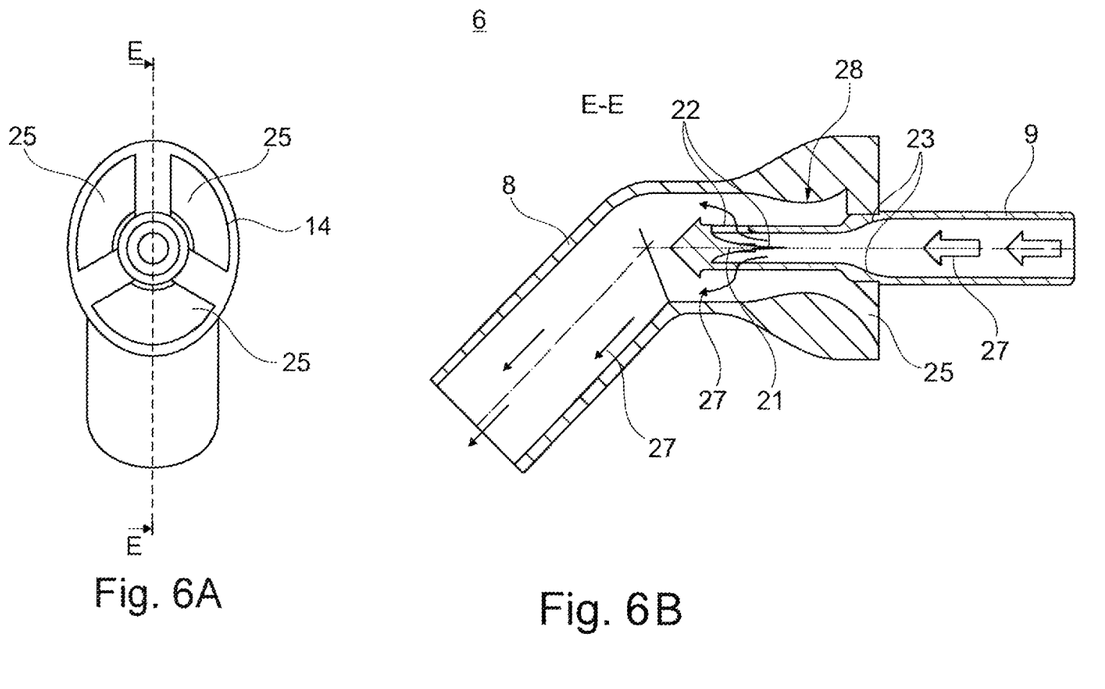
FIG. 6A illustrates a front view of the tracheal applicator as also illustrated in FIG. 4A.
FIG. 6B illustrates a full-width cut through the tracheal applicator taken along the line E-E FIG. 6A and having a sketched inspiration flow.

FIG. 6B illustrates a full-width section through the tracheal applicator (6) taken along the line E-E of FIG. 6A having a sketched inspiration flow, which is represented by the sketched flow arrows (27). The $FiO_2$ flow, which is generated by the TNI device and gets into the connecting piece (9) of the tracheal applicator (6) via the connecting tube (4) and the tube connection (17) (cf. FIG. 3), flows through the connecting piece (9), enters the adapter (8) through the outlet openings (22) and from there gets into the lungs via the connected tracheal cannula (7) (cf. FIG. 3). This occurs at a pressure which is 2 to 3 mbar above the atmospheric pressure in order to supply the alveoli of the lungs with enough breathing air. Since the pressure in the adapter (8) is slightly higher than the air pressure in the surrounding air, the proportion of the surrounding air inhaled via the ventilation openings (25) is fairly low. Owing to the inventive arrangement of the connecting piece (9) having the adapter (8), the tier-less bottleneck-shaped tapering (23) inducing a Venturi effect, and the conduction, caused by the contour (21), of the flow from the connecting piece (9) into the adapter (8), as well as owing to the inner bulge (28) in the trumpet-shaped opening (14) of the adapter (8), a sequence mostly free of vortexes results for the inspiration flow.

Figure 7A:
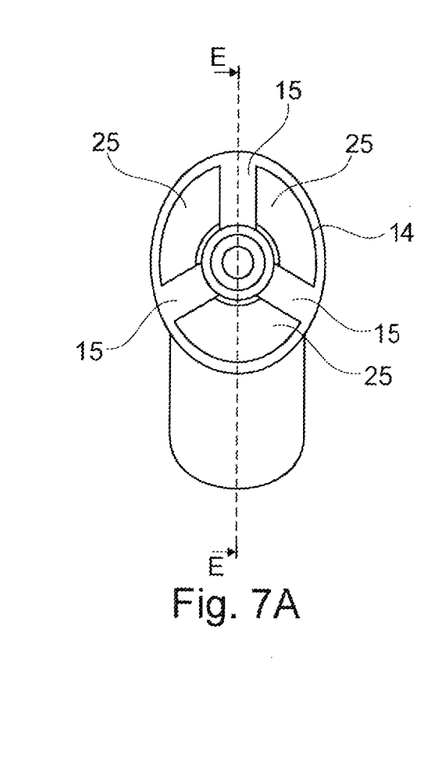
FIG. 7A illustrates a front view of the tracheal applicator as also illustrates in FIG. 4A.
Figure 7B:
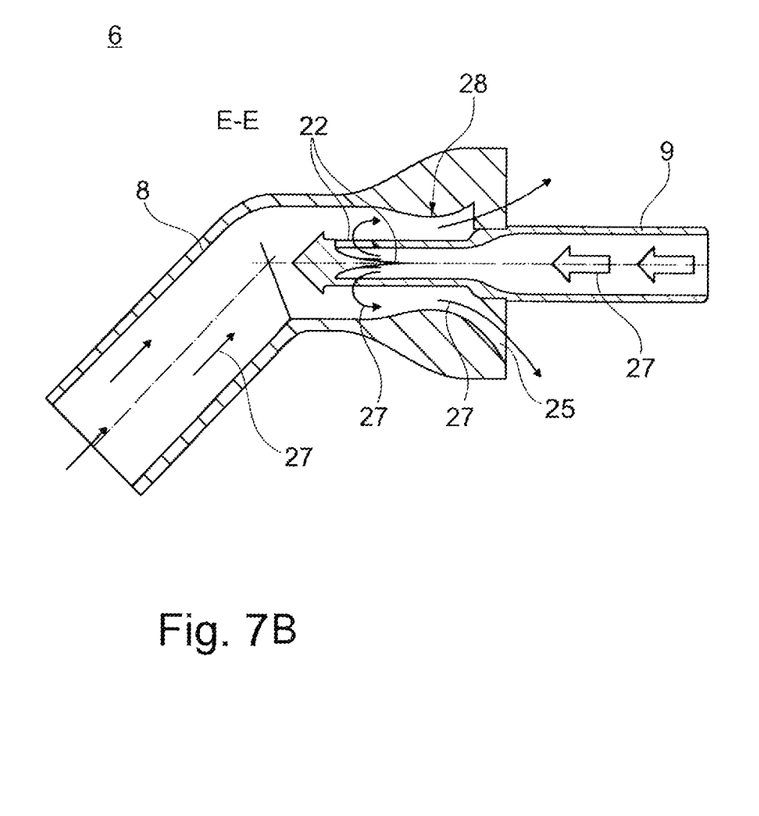
FIG. 7B illustrates a full-width cut through the tracheal applicator taken along the line E-E of FIG. 7A and having a sketched expiration flow.

FIG. 7B illustrates a full-width section through the tracheal applicator (6) taken along the line E-E according to FIG. 7A having a sketched expiration flow. When the patient exhales via the lungs, the pressure is 4 to 6 mbar above the pressure during inspiration. The spent and exhaled breathing air flows through the tracheal cannula (7) into the adapter (8) (cf. FIG. 3) and exits from the adapter (8) via the ventilation openings (25) of the trumpet-shaped opening (14). Since the pressure of the $FiO_2$ flow generated by the TNI device is lower in the exhalation phase than the pressure of the exhaled air, the $FiO_2$ flow continues to flow through the outlet openings (22) into the adapter (8) but it is then carried along by the exhaled breathing air and flows through the ventilation openings (25) in order to consequently be discharged into the environment. Owing to the acute profile of the crosspieces (15) (cf. FIG. 5), the expiration flow can escape free of vortexes in this instance.

The tracheal applicator (6) according to the invention can be made of any desired medical-grade plastic or can be provided with an antibacterial polymer coating.

LIST OF REFERENCES 1 nasal cannula
2 prongs
3 nostrils
4 connecting tube
5 TNI device/high flow therapy device
6 tracheal applicator
7 tracheal cannula
8 adapter
9 connecting piece
10 end
11 conical constriction
12 end
13 rotationally symmetric tube
14 trumpet-shaped opening
15 crosspieces
16 cylindrical contact surface
17 tube connection
18 center line
19 holder
20 seal
21 contour
22 outlet opening
23 bottleneck-shaped tapering
24 rounded edges
25 ventilation openings
26 access to temperature sensor
27 flow arrows
28 inner bulge
29 three-point reception

The invention claimed is:
1. A tracheal applicator:
wherein said applicator comprises a curved tube-shaped adapter having a circular diameter which at one end comprises a conical constriction, which protrudes into the interior of the adapter, for a plug-in connection with a tracheal cannula and at the other end is provided with a trumpet-shaped opening, three radially extending crosspieces protruding into the interior of the adapter in the trumpet-shaped opening in order to serve as a three-point reception for centrally holding and securing a connecting piece of the tracheal applicator and to simultaneously form three ventilation openings,
wherein the connecting piece comprises a rotationally symmetric tube constricted in a nozzle-like manner for channeling a $FiO_2$ flow coming from a high flow therapy device, a part of the connecting piece protruding into the adapter comprising a bottleneck-shaped tapering at one end of the connecting piece and being provided with a seal at the tapered end and comprising several radially distributed and radially extending outlet openings in direct contact with said seal, and the other end of the connecting piece being conically tapered in order to be coupled to a connecting tube of the high flow therapy device by pressing.

2. The tracheal applicator according to claim 1, wherein the edge of the trumpet-shaped opening is formed elliptical.

3. The tracheal applicator according to claim 2, wherein within the adapter, no outlet opening is provided which extends parallel to the longer symmetric axis of the elliptical shape of the trumpet-shaped opening and points in the direction of the apex of the elliptical shape closest to the conical constriction of the adapter.

4. The tracheal applicator according to claim 1, wherein the outlet openings have roundings at their edges.

5. The tracheal applicator according to claim 1, wherein the seal is formed conical in the direction of the adapter and comprises a tapered contour in the direction of a tube connection, said contour protruding into the interior of the connecting piece and serving as a flow conducting body.

6. The tracheal applicator according to claim 1, wherein the outer surfaces of the crosspieces are formed tapering towards the interior of the adapter.

7. The tracheal applicator according to claim 1, wherein the trumpet-shaped opening has an inner bulge.

8. The tracheal applicator according to claim 1, wherein the connecting piece comprises a cylindrical contact surface which serves for being connected to the three-point reception of the adapter.

9. The tracheal applicator according to claim 8, wherein the adapter and the connecting piece are connected at the contact points between the three-point reception and the cylindrical contact surface by clamping, by adhesion or by welding or in that the tracheal applicator is produced in one piece.

10. A tracheal ventilatory support system comprising:
a high flow therapy device comprising a connecting tube,
a tracheal cannula, and
a tracheal applicator according to claim 1, which connects the high flow therapy device and the tracheal cannula.

* * * * *

UNITED STATES PATENT AND TRADEMARK OFFICE
CERTIFICATE OF CORRECTION

Page 1 of 1

PATENT NO. : 10,478,577 B2
APPLICATION NO. : 16/071968
DATED : November 19, 2019
INVENTOR(S) : Dieter Klaus et al.

It is certified that error appears in the above-identified patent and that said Letters Patent is hereby corrected as shown below:

In the Specification

Column 4, Line 9, "4C an" should be --4C is an--.

Column 4, Line 22, "also illustrates in" should be --also illustrated in--.

Signed and Sealed this
Eighteenth Day of February, 2020

Andrei Iancu
*Director of the United States Patent and Trademark Office*